United States Patent [19]

Young et al.

[11] Patent Number: 5,449,608
[45] Date of Patent: Sep. 12, 1995

[54] PARVOVIRUS B19 RECEPTOR AND PARVOVIRUS B19 DETECTION

[75] Inventors: Neal S. Young, Washington, D.C.; Kevin E. Brown, Rockville, Md.

[73] Assignee: The United States of America as represented by the Department of Health and Human Services, Washington, D.C.

[21] Appl. No.: 34,132

[22] Filed: Mar. 22, 1993

[51] Int. Cl.$^6$ .................... G01N 33/569; C12N 7/00; C12Q 1/70

[52] U.S. Cl. ................................ 435/7.2; 435/235.1; 435/5

[58] Field of Search ............... 435/7.2, 235.1, 239, 435/240.1, 320.1, 5; 514/25; 536/4.1

[56] References Cited

PUBLICATIONS

Brown, K. E. & Cohen, B. J., *J. Gen. Virol.*, 73:2147–2149 (1992).
Yoshimoto, Kohji et al., "A Second Neutralizing Epitope of B19 Parvovirus Implicates the Spike Region in the Immune Response," *Journal of Virology*, 65(12):7056–7060 (Dec. 1991).
Sato, Hiroyuki et al., "Identification of the Region Including the Epitope for a Monoclonal Antibody Which Can Neutralize Human Parvovirus B19," *Journal of Virology*, 65(4):1667–1672 (Apr. 1991).
Young, N., *Semin. Hematol.*, 25:159–172 (1988).
von dem Borne, A. E., Bos, M. J., Joustra–Maas, N., et al., *Br J Haematol.*, 63:35–46 (1986).

*Primary Examiner*—Margaret Parr
*Assistant Examiner*—David Schreiber
*Attorney, Agent, or Firm*—Needle & Rosenberg

[57] ABSTRACT

The invention provides a method of detecting the presence of a parvovirus in a sample comprising contacting the sample with a purified receptor for a parvovirus, and detecting the presence of binding of parvovirus to the receptor, the presence of binding indicating the presence of parvovirus in the sample. The present invention also provides methods of purifying and removing parvoviruses from samples. The invention further provides a composition comprising a globoside, or the parvovirus B19 binding domain of globoside, in a pharmaceutically acceptable carrier. Also provided are methods of preventing or treating parvovirus B19 infection in a human subject by preventing the binding of parvovirus B19 to P antigen and methods of gene therapy utilizing parvovirus B19 and the parvovirus B19 cellular receptor.

5 Claims, No Drawings

PARVOVIRUS B19 RECEPTOR AND PARVOVIRUS B19 DETECTION

BACKGROUND OF THE INVENTION

1. Field of the Invention

The present invention relates to parvoviruses and to a cellular receptor for parvoviruses. Specifically, the invention relates to methods for detecting, preventing and treating infection of parvovirus, to methods of purifying and removing a parvovirus from samples, and to methods of gene therapy utilizing the parvovirus receptor.

2. Background Art

Parvoviruses are among the smallest DNA-containing viruses that infect animals and man. The parvoviridae family is divided into three genera: Parvovirus; Dependovirus (adeno-associated); and Densovirus. Parvoviruses range in size from 15 to 28 nm in diameter, lack a lipid membrane (non-enveloped), and contain a single strand of DNA. Parvoviruses are heat stable and generally resistant to chemical deactivating agents, which may account for their prevalence and persistence in the environment. In animals, many diseases such as canine parvovirus and feline panleukopenia exhibit high morbidity and high mortality in affected animal populations and the infections can persist endemically.

In man, the only known pathogenic member of this family is parvovirus B19. As with other parvoviruses, B19 is highly contagious and exhibits high morbidity in affected populations. Parvovirus B19 causes fifth disease in normal individuals (M. J. Anderson, et al. (1983)), transient aplastic crisis in patients with underlying hemolysis (N. S. Young; et al. (1988)), and chronic anemia due to persistent infection in immunocompromised patients (G. J. Kurtzman, et al. (1988) and N. Frickhofen et al. (1990)). Parvovirus infection in pregnancy can lead to hydrops fetalis and fetal loss (K. E. Brown (1989)) and/or congenital infection. B19 has also been implicated as the cause of chronic arthritis in adults where there is evidence of recent B19 infection, e.g., rheumatoid and inflammatory arthritis (B. J. Cohen et al. (1986) and D. G. White et al. There is currently no vaccine for protection from B19 infection.

B19 parvovirus exhibits extreme tropism for erythroid cells. Replication of B19 is restricted to human erythroid progenitor cells and the virus is dependent upon the presence of erythroprotein for replication in tissue culture systems (K. Ozawa et al. (1986) and K. Ozawa et al. (1987)). During B19 infection, the virus can be found in peripheral blood cells and the high levels of viremia seen with infection can lead to contamination of donor blood samples.

Despite the known pathogenicity of parvoviruses and the urgent need for methods to prevent, diagnose and treat parvovirus infections, a cell receptor has not been identified for any parvovirus. Early data suggested that the hemagglutinin of rodent parvoviruses might be a glycolipid (G. Cocuzza et al. (1969)), but similar studies suggest that feline panleukopenia virus binds to a glycoprotein on erythrocytes (M. Mochiziuki et al. (1978)). MVM (a rodent parvovirus) is thought to bind to a sialic acid containing glycoprotein, as pretreatment with neuraminidase or trypsin abolished binding (S. F. Cotmore et al. (1987)), and some evidence suggests that porcine parvovirus also binds to an undefined protein (M. J. Harding et al. (1992)). Even though there has been extensive study, the exact nature of the receptor is not known for any of the parvoviruses. Therefore a need exist to identify the cell receptors for parvoviruses and to provide a method for diagnosing, preventing and treating parvovirus infection utilizing the binding affinity for the receptor. Likewise, there exists a need to provide a method to purify and/or remove parvoviruses from samples. A cellular receptor for parvovirus also needs to be identified to assist researchers in searching for other species of parvoviruses and to aid in developing vaccines for parvoviruses.

The present invention satisfies that need by identifying a receptor for parvovirus B19 and by providing methods for diagnosis, treatment and prevention of B19 infection as well as methods for purification of B19 and methods of gene therapy utilizing the receptor for B19. Likewise, the methods utilized herein to identify the B19 receptor as well as the B19 receptor are applicable to other parvovirus receptors.

SUMMARY OF THE INVENTION

The present invention provides the discovery that an erythroid cell component (e.g., the glycolipid, globoside, or P antigen) is the cellular receptor for parvoviruses. In specific embodiments, the invention provides that globoside (globotetraosylceramide), or more particularly, the tetrahexoside, GalNAc($\beta$,1-3)Gal($\alpha$ 1-4) Gal($\beta$1-4)Glc, or a portion thereof, provides the specificity for binding parvovirus B19.

The present invention provides a method of detecting the presence of a parvovirus in a sample comprising contacting the sample with a purified receptor for a parvovirus, and detecting the presence of binding of parvovirus to the receptor, the presence of binding indicating the presence of parvovirus in the sample. This method can be utilized in any sample and thus is not limited to samples. The present invention further provides a composition comprising globoside bound to a substrate and provides a kit comprising at least two containers, wherein globoside or the parvovirus B19 binding domain of globoside bound to a substrate is in one container and an antibody specifically reactive with parvovirus B19 is in a separate container.

The invention also provides a method for separating a parvovirus from impurities in a sample and a method for removing a parvovirus from a sample. These methods comprise binding the parvovirus with a purified receptor for the parvovirus and separating or removing the bound parvovirus from the unbound portion of the sample. Likewise, the present invention provides a composition comprising a purified parvovirus receptor bound to the parvovirus.

The present invention also provides a composition comprising a globoside, or the pavovirus B19 binding domain of globoside, in a pharmaceutically acceptable carrier and provides the composition in an amount sufficient to administer to a human to treat or prevent an infection by parvovirus B19. Further, the present invention provides a method of preventing or treating parvovirus B19 infection in a human subject comprising preventing the binding of parvovirus B19 to P-antigen, thereby preventing infection of a cell by parvovirus B19 and preventing or treating parvovirus B19 infection. Parvovirus B19 binding can be prevented, for example, by administering globoside or the parvovirus B19 binding domain of globoside or by administering an antagonist including antibodies which bind P-antigen, thereby blocking the B19 binding domain.

Other embodiments of the present invention provide a human cell manipulated to have levels of P antigen on the cell surface which are increased over non-manipulated cells and a parvovirus B19 capable of infecting P-antigen containing cells, wherein the parvovirus B19 has a human derived gene inserted into the parvovirus B19 genome. Finally, the present invention provides a method of delivering a desired gene into a cell expressing the P antigen comprising infecting the cell with a parvovirus B19 having the desired gene inserted into the parvovirus B19 genome and a method of delivering a desired gene into a cell comprising increasing the amount of P antigen contained on the cell surface and infecting the cell with a parvovirus B19 having the desired gene inserted into the parvovirus B19 genome.

DETAILED DESCRIPTION OF THE INVENTION

The present invention may be understood more readily by reference to the following detailed description of specific embodiments and the Examples included therein.

As used in the claims, "a" can mean one or more.

The present invention provides the discovery that an erythroid cell component (e.g., the glycolipid, globoside or P antigen) is the cellular receptor for parvoviruses. Specifically, the invention provides that certain carbohydrates of these compounds provide the specificity for binding of parvoviruses to cells. For example, a tetrahexoside of globoside provides the specificity for binding of parvovirus B19 to human cells. Erythrocytes lacking P-antigen of the P blood group system cannot be agglutinated with B19. Purified P-antigen or globoside blocks binding of the virus to erythroid cells and therefore blocks the infectivity of the virus. Target cells can be protected from infection by preincubation with monoclonal anti-P antibody (A.E. von dem Borne et al. (1986)). This is the first identification of a parvovirus receptor, and there are important implications for pathogenesis, treatment, and the use of parvoviruses, for gene therapy.

The B19 parvovirus receptor was identified utilizing a hemagglutination (HA) assay as described in Brown and Cohen (1992). Briefly, the ability of B19 to hemagglutinate human red cells was utilized to evaluate the ability of certain compounds to inhibit agglutination in the assay. Cellular components from red cell membranes were fractionated and their reactivity evaluated in the HA assay. Lipid extraction and purification of glycolipid fractions followed by evaluation in the HA assay identified the glycosphingolipid, globoside, as the cellular receptor for B19. Further, biochemical characterization and HA evaluation identified the polysaccharide GalNAc($\beta$,3-3)Gal($\alpha$1-4)Gal($\beta$,1-4)Glc as the specific binding domain for B19. Verification of the receptor was accomplished utilizing in vitro infectivity assays, wherein globoside was used to competitively inhibit the cytotoxicity of B19 in erythroid cell lines. Antibodies specific for globoside were also utilized in the assay to block infectivity to verify that globoside was the receptor.

The methods of the present invention can be utilized to identify other parvovirus receptors. Specifically, parvovirus receptors that utilize short polysaccharide sequences, attached to lipid or protein components of the red cell membrane can be identified by the methods described herein.

The present invention provides a method of detecting the presence of a parvovirus in a sample comprising contacting the sample with a purified receptor for a parvovirus, and detecting the presence of binding of parvovirus to the receptor, the presence of binding indicating the presence of parvovirus in the sample. By "purified" is meant more pure than the compound exists in nature and pure enough for use in an assay, e.g., more pure than a cellular extract containing the receptor of choice. In a preferred embodiment of the present invention, a purified glycolipid, globoside, or the parvovirus B19 binding domain of globoside, is the receptor for parvovirus B19.

One example of a method of detecting parvovirus is performed by contacting a fluid or tissue sample from the subject with an amount of a purified receptor such as globoside or a B19 binding domain of globoside, e.g., GalNAc($\beta$1-3)Gal($\alpha$,1-4)Gal($\beta$,1-4)Glc, specifically reactive with the parvovirus, and detecting the binding of the receptor with the virus or an empty capsid of the virus. As contemplated herein, the purified receptor includes any ligand which binds the parvovirus, for example, an intact globoside or a fragment of globoside such as GalNAc($\beta$,1-3)Gal($\alpha$,1-4)Gal($\beta$, 1-4)Glc. The fluid sample of this method can comprise any body fluid which would contain the virus or a cell containing the virus, such as blood, plasma, serum, saliva and urine. Other possible examples of body fluids include sputum, mucus, gastric juice and the like.

Other fragments of globoside or the tetrahexoside, GalNAc($\beta$, 1-3)Gal($\alpha$,1-4)Gal($\beta$, 1-4)Glc which can be used in an assay or for therapy for parvovirus B19 can be determined by further cleavage of the fragment from the parent molecule, fractionating and testing the reactivity of the fragment in a binding assay, e.g., the HA assay as described above.

In one embodiment of the present invention, the presence of binding is determined by an immunoassay. Enzyme mediated immunoassays such as immunofluorescence assays (IFA), enzyme linked immunosorbent assays (ELISA) and immunoblotting assays can be readily adapted to accomplish the detection of the parvovirus bound to the receptor. An ELISA method effective for the detection of the virus can, for example, be as follows: (1) bind the receptor to a substrate; (2) contact the bound receptor with a fluid or tissue sample containing the virus; (3) contact the above with an antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect presence of the receptor as well as the virus.

Another immunologic technique that can be useful in the detection of parvoviruses is the competitive inhibition assay wherein parvovirus can be detected by competitive inhibition of receptor, e.g., globoside binding sites, utilizing monoclonal antibodies (MABs) specifically reactive with the receptor. Briefly, serum or other body fluids from the subject is reacted with the receptor bound to a substrate (e.g. an ELISA 96-well plate). Excess serum is thoroughly washed away. A labeled (enzyme-linked, fluorescent, radioactive, etc.) monoclonal antibody is then reacted with the previously reacted parvovirus virus-receptor complex. The amount of inhibition of monoclonal antibody binding is measured relative to a control. MABs can also be used for detection directly in samples by IFA for MABs specifically reactive for the receptor-virus complex.

Alternatively, a parvovirus and/or a patient's antibodies to the virus can be detected utilizing a capture assay. Briefly, to detect antibodies to parvovirus in a patient sample, antibodies to the patient's immunoglobulin, e.g., anti-IgG (or IgM) are bound to a solid phase substrate and used to capture the patient's immunoglobulin from serum. A parvovirus, or reactive fragments of a parvovirus, are then contacted with the solid phase followed by addition of a labeled receptor (e.g., globoside for a B19 assay). The amount of patient parvovirus specific antibody can then be quantitated by the amount of labeled receptor binding.

Additionally, a micro-agglutination test can also be used to detect the presence of parvovirus in test samples. Briefly, latex beads are coated with the receptor and mixed with a test sample, such that parvovirus in the tissue or body fluids that are specifically reactive with the receptor crosslink with the receptor, causing agglutination. The agglutinated receptor-virus complexes form a precipitate, visible with the naked eye or by spectrophotometer.

In the diagnostic methods described above, the sample can be taken directly from the patient or in a partially purified form. The receptor specific for a particular parvovirus (the primary reaction) reacts by binding to the virus. Thereafter, a secondary reaction with an antibody bound to, or labeled with, a detectable moiety can be added to enhance the detection of the primary reaction. Generally, in the secondary reaction, an antibody or other ligand which is reactive, either specifically or nonspecifically with a different binding site (epitope) of the receptor or the virus will be selected for its ability to react with multiple sites on the complex of receptor and virus. Thus, for example, several molecules of the antibody in the secondary reaction can react with each complex formed by the primary reaction, making the primary reaction more detectable.

The detectable moiety can allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, (1988)).

The present invention provides a composition comprising globoside or the parvovirus B19 binding domain of globoside bound to a substrate. Also provided is a kit comprising at least two containers, wherein globoside bound to a substrate or the parvovirus B19 binding domain of globoside bound to a substrate is in one container and an antibody specifically reactive with parvovirus B19 is in a separate container. By "specifically reactive" is meant an antibody which binds parvovirus B19 with sufficient specificity to allow for the detecting of B19. Such antibodies have been described in H. Sato et al., (1991) and K. Yoshimoto et al. (1991). Examples of suitable substrates include, but are not limited to, polymers, beads, latex plates and albumin. Other suitable substrates can be selected by referring to standard references, e.g., Harlow and Lane, *Antibodies: A Laboratory Manual*, Cold Spring Harbor Laboratory, Cold Spring Harbor, N.Y., (1988).

The bound globoside or diagnostic kit of the present invention can be used to detect the presence of a parvovirus specifically reactive with globoside or a reactive fragment thereof. The kit can also include a reagent for detecting a reaction of the antibody with the parvovirus. Such a kit can be an ELISA kit, including any other necessary detectable moieties, enzyme substrates or color reagents. Alternatively, an antibody specifically reactive with parvovirus B19 can be bound to a solid substrate and then contacted with parvovirus B19. One can then use globoside, or a fragment of globoside, to bind and detect parvovirus B19. Similar methods and modifications are described in Harlow and Lane, *Antibodies: A Laboratory Manual*, Cold Spring Harbor Laboratory, Cold Spring Harbor, N.Y., (1988). One skilled in the art can also appreciate that the kit of the present invention can also be designed for virus neutralization testing and/or capture immunoassays in the methods described herein for removal/purification of parvoviruses.

One embodiment of the present invention comprises a composition comprised of a purified parvovirus receptor, bound to the parvovirus. Specifically, the invention provides a composition comprising globoside or the parvovirus binding domain of globoside, e.g., GalNAc($\beta$1-3)Gal($\alpha$,1-4)Gal($\beta$,1-4)Glc bound to the parvovirus. The receptor can be a glycoprotein, glycolipid, ganglioside or a specific polysacharride moiety of such compounds which provides the specificity for binding. Contemplated herein are any compositions which contain the purified receptor or a portion thereof bound to a parvovirus. Examples of such compositions include but are not limited to test samples for diagnostic purposes, compositions utilized to remove impurities from a sample containing parvovirus, compositions for removing a parvovirus from a blood sample.

In a specific embodiment, the present invention provides a composition comprising a globoside, or the parvovirus B19 binding domain of globoside, in a pharmaceutically acceptable carrier. The invention also provides globoside, or the B19 binding domain in an amount sufficient to administer to a human to treat an infection by parvovirus B19. Treatment or prevention of B19 infection can be facilitated by competitive inhibition of the parvovirus by administration of exogenous globoside in a pharmaceutically acceptable carrier. The amount of globoside that would be sufficient to treat a parvovirus B19 infection in a human depends on the amount of globoside on the cells of the human subject. The dose can be determined by optimization procedures. A good starting point for determining a proper dose is to administer between about 8-12 times the quantity of globoside estimated to be present on the subject's red blood cells, e.g., an average male has about 395 $\mu$moles of globoside on his red cells and, therefore, would receive a starting dose of about 5 g of globoside. The amount of globoside will also vary depending upon the weight, size and health of the human subject and with the severity of B19 infection and can range from about 100 mg to about 10 grams. Thus, after administration of 5 g to various subjects, greater or lesser doses can be administered and the subject monitored for optimum efficacy.

In addition, given the discovery of P antigen as the cellular receptor for parvovirus B19, antagonists which specifically bind the P antigen and antagonize the binding of parvovirus B19 are also provided. The antagonist can be an antibody or a chemical which binds the receptor or otherwise alters the receptor or interferes with the interaction of virus and receptor. For example, utilizing methods known in the art, one can select a chemical which reacts with the tetrahexoside moiety of P antigen to antagonize binding of B19 to P antigen Empty. B19 capsids or the putative binding sites of B19 capsids, e.g., the VP2, major spike region, can be utilized as the antagonist. Alternatively, anti-idiotype and anti-anti-idiotype antibodies to both P antigen and the receptor binding region of parvovirus B19 can be utilized for prophylaxis or therapy. Naturally, the treatment modality can be selected to minimize any adverse side effects such as immune system recognition and deletion of the desirable P antigen containing cells. Thus, the invention also provides a method of screening for compounds which antagonize the binding of parvovirus B-19.

Depending on the intended mode of administration, the compounds of the present invention can be in pharmaceutical compositions in the form of solid, semi-solid or liquid dosage forms, such as, for example, tablets, pills, capsules, powders, liquids, and suspensions or the like, preferably in unit dosage form suitable for delivery of a precise dosage. The compositions will include, as noted above, an effective amount of the selected compound in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharin, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, latest edition (Mack Publishing Co., Easton, PA.)

Patients can also be treated orally with compositions of globoside or the parvovirus binding domain of globoside to block infection from enteric forms of B-19 or to block transmission of B19. For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

A presently preferred embodiment of the present invention comprises parenteral administration of the globoside or the B19 binding domain of globoside by intravenous injection. Injectables can be prepared in conventional forms, either as liquid solutions or suspensions, solid forms suitable for solution or suspension in liquid prior to injection, or as emulsions. Pharmaceutically acceptable carriers for parenteral administration include but are not limited to saline and the like.

The present invention also provides a method of preventing or treating parvovirus B19 infection in a human subject comprising preventing the binding of parvovirus B19 to P-antigen or other ligand, thereby preventing infection of a cell by parvovirus B19 and preventing or treating parvovirus B19 infection. The method further comprises preventing binding by administering to the subject a composition comprising globoside or the parvovirus binding domain of globoside which blocks the binding of parvovirus B19 to P-antigen or other ligand, thereby preventing or treating infection by the parvovirus in the subject. As previously stated, the amount of the composition used in the method will depend upon many factors including the route of administration, relative potency of the composition and size and health of the patient. It is contemplated herein that globoside or any portion of the globoside molecule, e.g., GalNAc($\beta$,1-3)Gal($\alpha$,1-4)Gal($\beta$,1-4)Glc, reactive with parvovirus B19 can be utilized in the method to treat or prevent infection by the parvovirus. Parvovirus B19 infection can also be prevented or treated by administering to the subject an antibody or other ligand reactive with P-antigen which blocks the B19 binding domain, e.g., the monoclonal antibody of A. E. von dern Borne et al. (1988). The amount of antibody administered will also be dependent upon the amount of P-antigen (globoside) on the cells of the subject and can be determined by optimization procedures as discussed herein.

It is also contemplated that other parvovirus infections can be prevented or treated in animals with other purified receptors reactive with the particular parvovirus species or with antbodies which bind the receptor. By utilizing methods of identification and purification of the receptor taught herein, one skilled in the art can identify other parvovirus receptors which can be utilized to prevent or treat parvovirus infections in other species. For example, the purified receptor for canine parvovirus can be utilized in a composition to prevent or treat infection or to block transmission of the virus in a canine utilizing methods for preparing the composition and optimization procedures for therapy described herein.

The present invention also provides a parvovirus B19 capable of infecting P antigen containing cells, wherein the parvovirus B19 has a human derived gene inserted into the parvovirus B19 genome. As a result of the discovery of the parvovirus B19 receptor, one skilled in the art can readily appreciate that parvovirus B19 or an attenuated strain can be utilized as a vector system to deliver parvovirus to P antigen expressing cells. Such methods are well known in the art and can be utilized by established procedures. (Sambrook et al., *Molecular Cloning: A Laboratory Manual*, 2nd Ed., Cold Spring Harbor Laboratory, Cold Spring Harbor, N.Y., (1989)).

The present invention also provides a human cell manipulated to have levels of P antigen on the cell surface which are increased over nonmanipulated cells. The cells contemplated herein can be manipulated to contain increased levels of P antigen, (globoside), GalNAc($\beta$,1-3)Gal($\alpha$, 1-4) Gal($\beta$1-4)Glc, or fragments thereof which act as a receptor for parvovirus B19. One skilled in the art can appreciate that these cells can be manipulated in many ways including direct addition of globoside to cells with subsequent incorporation by mass action into the lipid bilayer of the cell, or by chemical or enzymatic treatment of cells to either remove carbohydrates and expose P antigen specificity or to add carbohydrates to the lactosyl ceramide that is a common precursor of erythroid cells expressing the ABO as well as P antigen. The manipulated cells of the present invention can include cells originally non-permissive for parvovirus infection as well as permissive cells made more permissive. Examples of such cells include, but are not limited to, lymphocytes, hematopoietic stem cells or tumor cells.

The present invention also provides a method of delivering a desired gene into a cell comprising increasing the amount of P antigen contained on the cell surface and infecting the cell with a parvovirus B19 having the desired gene inserted into the parvovirus B19genome. Relatedly, the invention provides a method of delivering a desired gene into a cell expressing the P antigen comprising infecting the cell with a parvovirus B19 having the desired gene inserted into the parvovirus B19 genome. One skilled in the art will readily appreciate that the identification of P antigen (globoside) as the parvovirus B19 receptor, as taught by the present invention, enables methods of gene therapy with B19 as the vector system. The desired human DNA fragment can be easily inserted into a host cell, e.g., one with sufficient levels of P antigen on the cell surface as discussed herein utilizing methods known in the art, for example, See Nienhuis, A. W., et al., Marcel Dekker, New York (1993).

Another embodiment of the present invention provides a method of separating a parvovirus from impurities in a sample comprising binding the parvovirus with a purified glycolipid receptor for the parvovirus and separating the bound parvovirus from the unbound impurities in the sample, thereby separating the parvovirus from impurities in the sample. One skilled in the art will appreciate based on the teaching herein, that purification of parvovirus B19 and other parvoviruses can be accomplished by the use of immobilized carbohydrate sequences, e.g., GalNAc($\beta$, 1-3)Gal($\alpha$,1-4)Gal($\beta$,1-4)Glc, glycolipids such as globoside, or glycoproteins specifically reactive with the target parvovirus. Once a complex of receptor and virus is formed the impurities in a sample can be separated using techniques well known in the art and set forth herein.

Finally, the present invention provides a method for removing a parvovirus from a blood sample comprising binding the parvovirus in the blood with a purified glycolipid receptor for the parvovirus and separating the bound parvovirus from the blood, thereby removing the parvovirus from the blood sample. Donated blood contaminated with parvovirus B19 is especially dangerous for immunocompromised recipients. The method of the present invention utilizes the receptor for parvovirus, e.g., globoside for strain B19, to bind to the virus. The bound complex is removed from the blood sample by preparing a column with the immobilized receptor, e.g., globoside or the parvovirus binding domain of globoside. The sample is then passed through the column, thereby removing parvovirus from the sample utilizing the binding affinity for the receptor. Alternatively, the immobilized receptor can be mixed with the sample and the bound virus-receptor complex can be removed by centrifugation.

The present invention is more particularly described in the following examples which are intended as illustrative only since numerous modifications and variations therein will be apparent to those skilled in the art.

Throughout this application, various publications are referenced. The disclosures of these publications in their entire ties are hereby incorporated by reference into this application in order to more fully describe the state of the art to which this invention pertains.

EXAMPLES

To identify the B19 cellular receptor, the ability of B19 to agglutinate red cells and B19 infectivity assays were used as measures of viral binding. It had been previously shown that B19 parvovirus empty capsids (S. Kajigaya et al. (1991)) agglutinate human red cells Brown and Cohen (1992)), and we tested the ability of membrane extracts from different cell types to block B19 binding in the hemagglutination assay (HA). Membrane extracts were prepared using 10 mM CHAPS (3-[(3cholamidopropyl)-dimethylammonio]-1-propane-sulfonate) to solubilize proteins and lipids.

In order to characterize the physical nature of the B19 receptor, human red cells were treated with a variety of agents and the change in hemagglutination (HA) titer measured (ICE. Brown et al. (1992)) (Table 1). Trypsin and neuraminidase each increased binding, suggesting that protein and sialic acid were not involved in binding and that modification of the red cell membrane by these agents might expose binding sites. High concentrations (10 mM) of sodium periodate markedly reduced binding of virus to the erythrocytes (>4 $\log_2$ decrease in HA titer), implicating carbohydrates other than neuraminic acid. Phosphoinositol-specific phospholipase C and reducing agents did not affect binding.

TABLE 1

| Agent | Time | Final Conc. | Change in HA titer ($\log_2$) |
|---|---|---|---|
| Trypsin | 1 hr | 0.2% | +4 |
| Pronase | 1 hr | 100 U/ml | −1 |
| Dithiothreitol | 1 hr | 4 mM | 0 |
| 2-Mercaptoethanol | 1 hr | 5 mM | 0 |
| EDTA | 1 hr | 5 mM | 0 |
| Formaldehyde | 1 hr | 0.2% | 0 |
| PI specific phospholipase C | 20 hr | 5 U/ml | −1 |
| NaIO$_4$ | 20 hr | 5 uM | −1 |
| NaIO$_4$ | 15 min | 10 mM | <−4 |
| Neuraminidase | 15 min | 1 U/ml | +3 |
| Neuraminidase | 15 min | 0.1 U/ml | +3 |
| Neuraminidase | 15 min | 0.03 U/ml | +2 |

Table 1. Washed erythrocytes (0.5% v/v) were incubated at 37° C. with the reagents, washed twice in saline and resuspended at 0.5%. The cells were used in a standard hemagglutination assay using B19 empty capsids produced in insect cells (Brown and Cohen (1992)) the end point was 50% HA (1 HA$_{50}$). In the table, therefore, an increasing the HA titer ($\log_2$) by a factor of one reflects a doubling of the measured titer.

Further characterization of the receptor was performed using red cell membrane extracts. Selective solubilization of proteins and lipids produced a red cell extract that inhibited hemagglutination. Extracts from cells permissive for B19 (human bone marrow and UT-7 leukemic cells) (S. Shimomura et al. (1992)) also blocked agglutination, whereas extracts from K562, HL-60, and HeLa cells, which are not permissive for the virus, did not block binding. Pretreatment of extract with immobilized phospholipase $A_2$ removed activity, whereas treatment with immobilized proteases had minimal effect suggesting that the receptor was a lipid (Table 2). In addition, the hemagglutination inhibitor also partitioned into the organic phase of a water:-butanol mixture and the lower or lipid phase of a chloroform/methanol:salt solution mixture ("Folch" extract, J. Folch et al. (1957)).

TABLE 2

| Material | HAI titer |
| --- | --- |
| CHAPS extract treated with: | |
| Saline (control) | 1280 |
| Trypsin | 640 |
| Protease Sg | 640 |
| Lipase | 640 |
| Phospholipase $A_2$ | <10 |
| Purified glycosphingolipid | |
| Lactosyl ceramide (1 mg/ml) | <10 |
| CTH, $P^k$ (1 mg/ml) | <10 |
| Globoside, P (1 mg/ml) | 25600 |
| Forssman (1 mg/ml) | 200 |

Table 2. Human erythrocyte ghosts (J. T. Dodge, et al (1963)) were treated with 10 mM CHAPS, the solubilized extract incubated with agarose immobilized enzymes overnight at 37° C. and the supernatant tested in a hemagglutination inhibition assay (HAI). Purified glycosphingolipids (Sigma or BioCarb Chemicals) were dissolved in saline and tested by HAI using 4–8 $HA_{50}$ units of virus capsid. (In the table, CTH is ceramide trihexoside and the HAI titer is the dilution required to reduce the HA to 50% (1 $HA_{50}$ Unit)).

Confirmation that the inhibitor activity was in the lipid fraction was obtained by preparing a pure lipid extract (Rose et al. (1965)) followed by fractionation on either a silica gel column or DEAE-cellulose-acetate (W. Christie et al. (1987)). Inhibitor activity eluted with methanol or 1:1 chloroform:methanol respectively, properties consistent with a ceramide oligohexoside (Table 3). A mixture of purified ceramide oligohexosides inhibited hemagglutination by the virus. Assays of individual glycolipids showed that the inhibitory activity was due to a ceramide tetrahexoside, globotetraosylceramide (or globoside, GalNAc($\beta$,1-3)Gal($\alpha$,1-4)Gal(fi, 1-4)Glc-Cer).

TABLE 3

| Eluent | Lipids eluted | HAI titer |
| --- | --- | --- |
| Silica gel column | | |
| Chloroform | simple lipids | <10 |
| Acetone | glycolipids | <10 |
| Methanol | ceramide oligohexosides polar lipids | 2560 |
| DEAE-cellulose-acetate column | | |
| Chloroform | simple lipids | 80 |
| 9:1 chloroform:methanol | ceramide monohexoside phosphatidylcholine | 640 |
| 1:1 chloroform:methanol | ceramide oligohexoside | 1280 |
| Methanol | — | <10 |
| Acetic acid | phoshatidylserine | <10 |
| Ammonium acetate | phosphatidylinositol | <10 |

TABLE 3-continued

| Eluent | Lipids eluted | HAI titer |
| --- | --- | --- |
| | phospatidylglycerol | |

Table 3. Hemagglutination inhibition (HAI) titers red cell lipid fractionated on different columns. Lipid was extracted from red cell ghosts (9,12) and fractionated on either a silica gel or DEAE-cellulose-acetate column (13). Organic solvents were removed by evaporation and salts removed by dialysis against water and lyophilization. The residual pellets were resuspended in saline and tested in the hemagglutination assay.

The P blood group system was discovered in 1927 by Landsteiner and Levine (Landsteiner et al. (1927)) and contains two common antigens, $P_1$ and P, and the much rarer $p^k$ antigen The $p^k$ antigen or ceramide trihexoside (CTH, globotriaosylceramide, Gal(a,1-4)Gal(b,1-4)Glc-Cer) is a normal precursor of P, which was identified as globoside. ($P_1$ antigen is an unrelated lactoneotetraose ceramide derivative). Red cells of individuals with blood group $P_1$ phenotype have $P_1$ and P antigens; individuals with $P_1^k$ phenotype have $P_1$ and $P^k$ antigens; individuals with $P_2$ phenotype have P antigen alone; and individuals with the rare p phenotype lack all three antigens (D. M. Marcus et al. (1981)). Forssman antigen is not a normal constituent of human cells but a pentahexoside containing the same saccharide sequence as globoside with an added terminal N-acctylgalactosamine residue.

Red cells from individuals with different blood group P system phenotypes were tested for their ability to agglutinate with parvovirus B19. Only cells containing P antigen hemagglutinated: $P_1$ phenotype HA titer was 10,000; $P_2$ phenotype HA titer was 5,000; $P_1^k$ and p phenotype were <200. Binding of viral capsids to globoside was demonstrated by thin layer chromatography. Lipids were extracted from 0.2 mls packed red cells (H. Rose et al. (1965)) of patients with different P blood group phenotypes, dried and resuspended in 50 ul chloroform:methanol 1:1.20 ul of extract or 1 ug of each purified glycosphingolipid (Calbiochem) were applied to a silica plate (Merck) and chromatography performed with chloroform:methanol:water 65:25:4. Non-specific binding was blocked with 3% bovine albumin in phosphate buffered saline (16 hours) before the plates were sequentially incubated with B19 empty capsids, a human polyclonal anti-B19 serum, goat anti-human antibody conjugated with horse radish peroxidase, and developed with diaminobenzidene enhanced with cobalt chloride. The capsids bound to the globoside in $P_1$ and $P_2$ cells, and to purified globoside and Forssman antigen. B19 capsids and mouse monoclonal antibody to globoside (A. E. von dem Borne et al. (1986)) bound to the same band on Western blotting of red cell extract, the putative "globoprotein" (Y. Tonegawa et al. (1977)). However this band could be removed by digestion with lipase but not by proteases indicating that this also was glycolipid.

To establish the biological relevance of binding of virus to P antigen, globoceramides were tested for their ability to block vital infection of permissive cells, using the erythroid progenitor assay (P. P. Mortimer et al. (1983)). Parvovirus B19 is highly toxic to the production of erythroid colonies from late erythroid progenitors (CFU-E) in methylcellulose culture, and this system was used as an assay for B19 infection. In the study, binding of B19 antigen to P antigen was shown by competition of infection using globoside or monoclonal antibody to P antigen. First, B19 virus was preincubated with different globoceramides, e.g., lactosyl, triosyl, and Forssman (Sigma or BioCarb Chemicals) and with different globoside concentrations for two hours, and then mixed with bone marrow mononuclear cells for a further two hours. There was a positive linear relationship in globoside's ability to block infectivity of the mononuclear cells with B19 virus, e.g., as the concentration of globoside increased the greater the inhibition of cytotoxicity. In the erythroid progenitor assay, B19 cytotoxicity was completely blocked by addition of globoside; there was less protection with Forssman antigen and no effect by other oligoceramides (CTH or CDH, ceramide dihexoside). Second, mouse monoclonal antibodies to P-antigen (A. E. yon dem Borne et al. (1986)) or $P_1$ or $p^k$ (BioCarb Chemicals) were diluted 1:100 and incubated with bone marrow mononuclear cells for two hours. Purified B19 virus as above was added for a further two hours. The cell mixtures were plated in methylcellulose (P. Mortimer et al. (1983)) and CFU-E counted seven days later. Infection was completely blocked by preincubation of target cells with monoclonal antibody specific to globoside. There was no protection with similar antibodies against $P_1$ or $p^k$.

These findings show that B19 capsids bind to P-antigen and that B19 infection can be blocked by excess globoside or globoside-specific monoclonal antibody. These results demonstrate that P antigen is the B19 virus receptor. The four-carbohydrate chain, GalNAc($\beta$,1-3)Gal($\alpha$,1-4)Gal($\beta$,1-4)Glc, mediates binding specifically, as ceramides with different saccharide chains do not have this effect.

P antigen is present not only on cells that are permissive for infection but also on other cells, such as endothelial cells, which may be the targets of viral infection important in transplacental transmission and in the rash of fifth disease. Paroxysmal cold hemoglobinuria, the most common immune hemolytic anemia of childhood, is characterized by anti-P antibody (P. Levine et al. (1963)) and may be a sequela of B19 parvovirus infection. Individuals of the blood group phenotype p, who lack P antigen, may not be susceptible to parvovirus infection. Finally, recent data suggest that Amish individuals who genetically lack the P antigen receptor are not susceptible to B19 infection. Bone marrow from these individuals who lack P antigen cannot be infected in vitro by B19. Likewise, individuals who lack P antigen consistently do not exhibit antibody tilers against B19.

Although the present process has been described with reference to specific details of certain embodiments thereof, it is not intended that such details should be rcgarded as limitations upon the scope of the invention except as and to the extent that they are included in the accompanying claims.

REFERENCES

1. Anderson, M. J., Jones, S. E., Fisher-Hoch, S. P., et al., *Lancet, i:*1378–1378 (1983).
2. Brown, K. E., *Br. J. Obstet. Gynaecol.,* 96:764–767 (1989).
3. Brown, K. E. & Cohen, B. J., *J. Gen. Virol.,* 73:2147–2149 (1992).
4. Christie, W. W., "High-Performance Liquid Chromatography and Lipids," Oxford: Pergamon Press, 81–85 (1987).
5. Cocuzza, G. & Russo, G., Boll. 1*st. Sieroter. Milan.,* 48:204–206 (1969).
6. Cohen, B. J., Buckley, M. M., Clewley, J. P. et al., "Human Parvovirus Infection in Early Rheumatoid and Inflammatory Arthritis," *Ann. Rheum. Dis.,* 45:832–838 (1986).
7. Cotmore, S. F. & Tattersall, P., *Adv. Virus. Res.,* 33:91–174 (1987).
8. Dodge, J. T., Mitchell, C. & Hanahan, D. J., *Arch. Biochem. Biophys.,* 110:119–130 (1963).
9. Folch, J., Lees, M. & Sloane Stanley, G. H., *J. Bid. Chem.,* 226:497–509 (1957).
10. Frickhofen, N., Abkowitz, J. L., Safford, M., et al., *Ann. Intern. Med.,* 113:926–933 (1990).
11. Harding, M. J. & Molitor, T. W., *Arch. Virol.,* 123:323–333 (1992).
12. Harlow and Lane, *Antibodies: A Laboratory Manual,* Cold Spring Harbor Laboratory, Cold Spring Harbor, N.Y. (1988).
13. Kajigaya, S., Fujii, H., Field, A., et al., *Proc. Natl. Acad. Sci. U.S. A.* 88:4646–4650 (1991).
14. Kurtzman, G. J., Cohen, B., Meyers, P., Amunullah, A. & Young, N. S., *Lancet,ii:*1159–1162 (1988).
15. Landsteiner, K. & Levine, P., *Proc. Soc. Exp. Bid. Med.,* 24:941–942 (1927).
16. Levine, P., Cclano, M. J. & Falkowski, F., *Transf.,* 3:278–280 (1963).
17. Liu, J. M., Green, S. W., Shimada, T. & Young, N. S., *J Virol.,* 66:4686–4692 (1992).
18. Marcus, D. M., Kundu, S. K. & Suzuki, A., *Semin. Hematol.,* 18:63–71 (1981).
19. Martin, E. W. (ed.) Remington's Pharmaceutical Sciences, latest edition, Mack Publishing Co., Easton, Pa. Mochizuki, M., Konishi, S. & Ogata, M., *Nippon Juigaku. Zasshi,* 40:375–383 (1978).
20. Mortimer, P. P., Humphries, R. K., Moore, J. G., Purcell, R. H. & Young, N. S., *Nature,* 302:426–429 (1983).
21. Ozawa, K., Kurtzman, G., Young, N., "Productive Infection by B19 Parvovirus of Human Erythroid Bone Marrow Cells *In Vitro,*" *Blood,* 70:384–391 (1987).
22. Ozawa, K., Kurtzman, G., Young, N, "Replication of the B19 Parvovirus in Human Bone Marrow Cultures," *Science,* 233:883–886 (1986).
23. Rose, H. G. & Oklander, M., *J. Lipid Res.,* 6:428–431 (1965).
24. Sato, Hiroyuki et al., "Identification of the Region Including the Epitope for a Monoclonal Antibody Which Can Neutralize Human Parvovirus B19 "*Journal of Virology,* 65(4):1667–1672 (April 1991).
25. Shimomura, S., Komatsu, N., Frickhofen, N., Anderson, S., Kajigaya, S.& Young, N. S., *Blood,* 79:18–24 (1992).
26. Tonegawa, Y.& Hakomori, S., *Biochem. Biophys. Res. Com.,* 76:9–17 (1977).
27. von dem Borne, A. E., Bos, M. J., Joustra-Maas, N., et al., *Br J Haematol.,* 63:35–46 (1986).
28. Walsh, C. E., Liu, J. M., Xiao, X., Young, N. S., Nienhuis, A. W. & Samulski, R. *J., Proc. Natl. Acad. Sci. U.S. A.,* 89:7257–7261 (1992).
29. White, D. G., Mortimer, P. P., Blake, D. R. et al., "Human Parvovirus Arthropathy," *Lancet,* 1:419–421 (1985).
30. Yoshimoto, Kohji et al., "A Second Neutralizing Epitope of B19 Parvovirus Implicates the Spike Region in the Immune Response," *Journal of Virology,* 65(12):7056–7060 (December 1991).
31. Young, N., *Semin. Hematol.,* 25:159–172 (1988).

What is claimed is:

1. A method of detecting the presence of a parvovirus B19 in a sample comprising:

a) contracting the sample with purified globoside or the parvovirus B19 binding domain of globoside the purified globoside or parvovirus B19 binding domain or globoside being separated from a cell that contains globoside; and b) detecting the presence of specific binding of paravovirus B19 to the globoside or the parvovirus B19 binding domain of globoside, the presence of specific binding indicating the presence of parvovirus B19 in the sample.

2. The method of claim 1 wherein B19 binding domain is GalNAc($\beta$,1-3)Gal($\alpha$,1-4)Gal($\beta$, 1-4)Glc.

3. The method of claim 1 wherein the sample is a tissue sample.

4. The method of claim 1 wherein the sample is a blood sample.

5. The method of claim 1 wherein the presence of binding is determined by an immmunoassay.

* * * * *